(12) United States Patent
Kaula

(10) Patent No.: US 11,420,053 B2
(45) Date of Patent: Aug. 23, 2022

(54) DIAGNOSTIC, NEUROSTIMULATING, AND THERAPEUTIC METHOD APPLIED TO BIOLOGICAL TARGETS THAT ARE NATURALLY INTEGRATED TO EACH OTHER

(71) Applicant: Norbert Kaula, Arvada, CO (US)

(72) Inventor: Norbert Kaula, Arvada, CO (US)

( * ) Notice: Subject to any disclaimer, the term of this patent is extended or adjusted under 35 U.S.C. 154(b) by 150 days.

(21) Appl. No.: 17/001,577

(22) Filed: Aug. 24, 2020

(65) Prior Publication Data

US 2021/0052891 A1 Feb. 25, 2021

Related U.S. Application Data

(60) Provisional application No. 62/890,580, filed on Aug. 22, 2019.

(51) Int. Cl.
*A61N 1/36* (2006.01)
*A61N 1/05* (2006.01)

(52) U.S. Cl.
CPC ....... *A61N 1/36007* (2013.01); *A61N 1/0558* (2013.01); *A61N 1/36062* (2017.08)

(58) Field of Classification Search
CPC .............. A61N 1/36007; A61N 1/0558; A61N 1/36062; A61N 1/0556; A61N 1/0551
See application file for complete search history.

(56) References Cited

U.S. PATENT DOCUMENTS

2011/0071590 A1* 3/2011 Mounaim .......... A61N 1/36007
607/41
2015/0173918 A1* 6/2015 Herr ..................... A61N 1/0551
623/25

* cited by examiner

*Primary Examiner* — Paula J Stice
(74) *Attorney, Agent, or Firm* — George Guosheng Wang; Upstream Research and Patent LLC

(57) ABSTRACT

The present invention provides a method for coordinated neurostimulation of two or more biological targets are naturally integrated to each other such as nerves. The method includes disintegrating and separating the two or more biological targets from each other; and wrapping an electrode device around the separated biological targets. The electrode device may include suture holes, and the method, further includes a step of stitching the electrode device around the biological targets through the one or more suture holes. The electrode in the electrode device can electrically and stably contact the biological targets.

17 Claims, 11 Drawing Sheets

DIAGNOSTIC, NEUROSTIMULATING, AND THERAPEUTIC METHOD APPLIED TO BIOLOGICAL TARGETS THAT ARE NATURALLY INTEGRATED TO EACH OTHER

CROSS-REFERENCE TO RELATED APPLICATIONS

This application expressly claims the benefits and priority based on U.S. Provisional Application No. 62/890,580 filed Aug. 22, 2019, which is incorporated herein by references as if set forth in its entirety.

FIELD OF THE INVENTION

The present invention generally relates to a diagnostic, neurostimulating, and/or therapeutic method applied to biological targets that are naturally integrated to each other. In general embodiments, provided are a method for coordinated stimulation of two or more integrated nerve components, and a lead, a device and a system designed for executing said method. Although the invention will be illustrated, explained and exemplified with a coordinated stimulation of anterior and posterior spinal nerve components for bladder control using a flap-shaped or ribbon-shaped lead, it should be appreciated that the present invention can also be applied to other integrated nerve components using other types of lead to treat other medical symptoms.

BACKGROUND OF THE INVENTION

Neurostimulation in medicine is a modulation of the nervous system's activity using invasive (e.g. microelectrodes) or non-invasive means (e.g. transcranial magnetic stimulation or transcranial electric stimulation, tES, such as tDCS or transcranial alternating current stimulation, tACS). Neurostimulation is particularly helpful for patients who are severely paralyzed or suffering from losses to functionality, such as movement of extremities or loss of internal organ functions. In the case of neural stimulation, mostly an electrical stimulation is utilized, and constant current waveform approaches are adopted.

For example, Giles Brindley introduced the first surgical implant to evacuate the bladder in paraplegic patients by directly stimulating intradurally the efferent nerves AND pertaining a rhizotomy (cutting) of the afferent nerves, that otherwise would inhibit the induced bladder contraction. Please see "Sacral anterior roots stimulation for bladder control" in Paraplegia 20:365-381, 1982. Other related references include J. Kutzenberger, B. Domurath, and D. Sauerwein, Spastic bladder and spinal cord injury: seventeen years of experience with sacral deafferentation and implantation of an anterior root stimulator, Artif Organs, 29(3) 239-41, March 2005; and Extradural implantation of sacral anterior root stimulator in spinal cord injury patients Castaño-Botero, Juan Carlos and Ospina-Galeano, Irma Amparo and Gómez-Illanes, Reynaldo and Lopera-Toro, Adrian Neurourol Urodyn 2016, 35/8, 970-974.

Advantageously, the present invention provides an improved diagnostic, neurostimulating, and therapeutic method applied to biological targets that are naturally integrated to each other. In an exemplary embodiment, the present invention introduces a special electrode that will achieve a similar or better result without cutting nerves.

SUMMARY OF THE INVENTION

One aspect of the present invention provides diagnostic, neurostimulating, and/or therapeutic method, comprising (i) providing a medical device or system comprising a flexible and implantable electrode device; (ii) determining or locating two or more biological targets in a patient, wherein the two or more biological targets are naturally integrated to each other; (iii) disintegrating and separating the two or more biological targets from each other; (iv) wrapping the electrode device around one or more of the separated biological targets, so that at least one electrode in the electrode device can electrically and stably contact the biological target(s); and (v) executing a diagnostic and/or therapeutic process on the biological target(s).

Another aspect of the invention provides a medical device or system as used in the diagnostic, neurostimulating, and/or therapeutic method described above.

The above features and advantages and other features and advantages of the present invention are readily apparent from the following detailed description of the best modes for carrying out the invention when taken in connection with the accompanying drawings.

BRIEF DESCRIPTION OF THE SEVERAL VIEWS OF THE DRAWINGS

The present invention is illustrated by way of example, and not by way of limitation, in the figures of the accompanying drawings and in which like reference numerals refer to similar elements. All the figures are schematic and generally only show parts which are necessary in order to elucidate the invention. For simplicity and clarity of illustration, elements shown in the figures and discussed below have not necessarily been drawn to scale. Well-known structures and devices are shown in simplified form, omitted, or merely suggested, in order to avoid unnecessarily obscuring the present invention.

DETAILED DESCRIPTION OF THE PREFERRED EMBODIMENT

In the following description, for the purposes of explanation, numerous specific details are set forth in order to provide a thorough understanding of the present invention. It is apparent, however, to one skilled in the art that the present invention may be practiced without these specific details or with an equivalent arrangement.

Where a numerical range is disclosed herein, unless otherwise specified, such range is continuous, inclusive of both the minimum and maximum values of the range as well as every value between such minimum and maximum values. Still further, where a range refers to integers, only the integers from the minimum value to and including the maximum value of such range are included. In addition, where multiple ranges are provided to describe a feature or characteristic, such ranges can be combined.

It is also to be understood that the terminology used herein is for the purpose of describing particular embodiments only, and is not intended to limit the scope of the invention. For example, when an element is referred to as being "on", "connected to", or "coupled to" another element, it can be directly on, connected or coupled to the other element or intervening elements may be present. In contrast, when an element is referred to as being "directly on", "directly connected to", or "directly coupled to" another element, there are no intervening elements present.

Figure 1A:
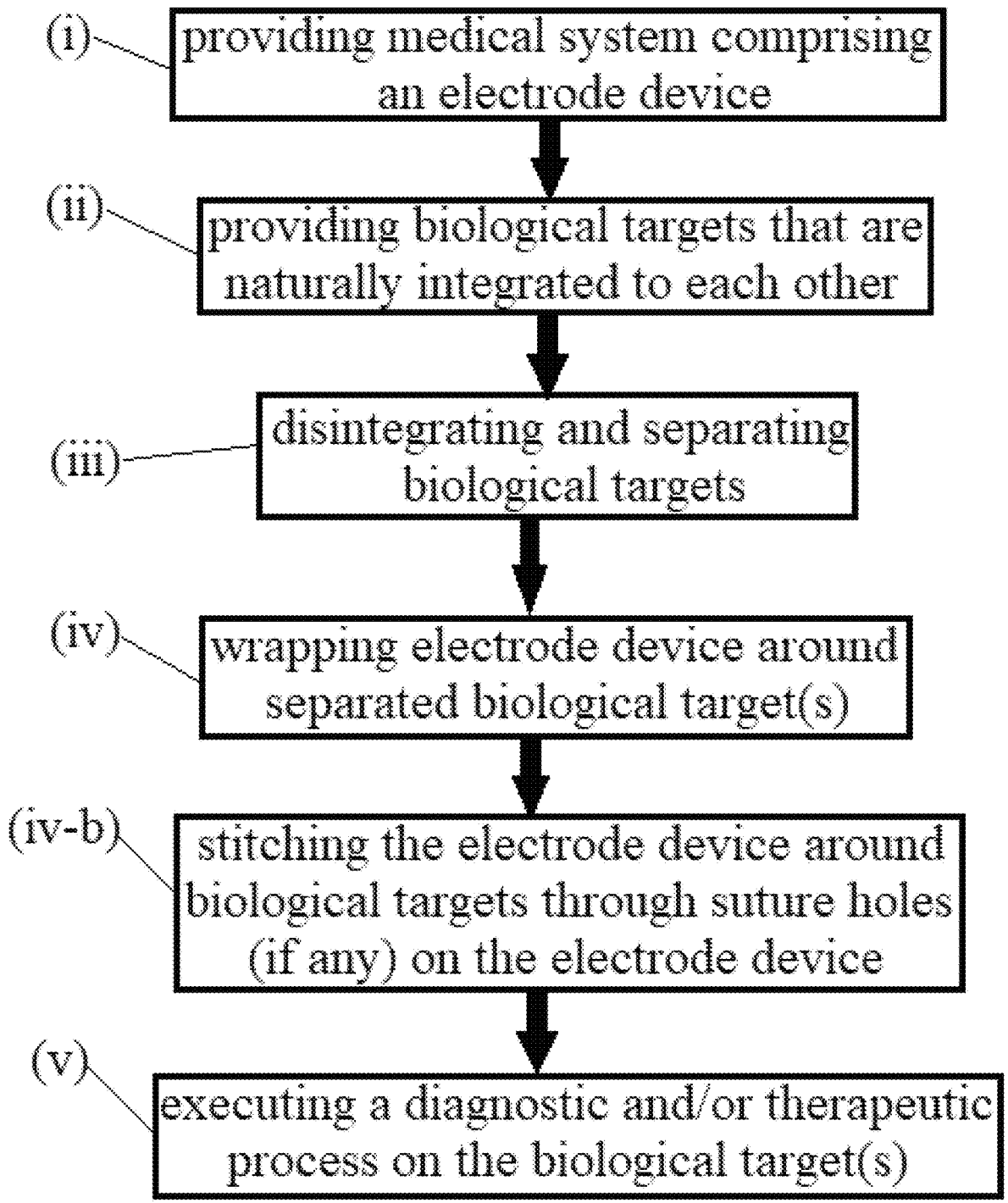
FIG. 1A is a flow chart of the diagnostic, neurostimulating, and/or therapeutic method in accordance with an exemplary embodiment of the present invention.

With reference to FIG. 1A, a general diagnostic, neurostimulating, and/or therapeutic method of the invention includes (i) providing a medical device or system comprising a flexible and implantable electrode device; (ii) determining or locating two or more biological targets in a patient, wherein the two or more biological targets are naturally integrated to each other; (iii) disintegrating and separating the two or more biological targets from each other; (iv) wrapping the electrode device around one or more of the separated biological targets, so that at least one electrode in the electrode device can electrically and stably contact the biological target(s); and (v) executing a diagnostic and/or therapeutic process on the biological target(s).

In a preferred yet exemplary embodiment, the implantable electrode device comprises one, two or more suture holes, and the method further includes an optional step of (iv-b) stitching the implantable electrode device around the one or more biological targets through the one or more suture holes after step (iv) but before step (v).

In various embodiments of the invention, the two or more biological targets are naturally integrated to each other by connecting through a connective tissue. Alternatively, they may be naturally integrated to each other by encapsulating together inside a same confinement made of connective tissue. For example, an anterior segmental nerve (ASN) and a posterior segmental nerve (PSN) may be encapsulated together within an epineurium. As a result, step (iii) of disintegrating and separating the two or more biological targets from each other may be carried out by cutting the epineurium (e.g. a laminectomy).

Figure 1B:
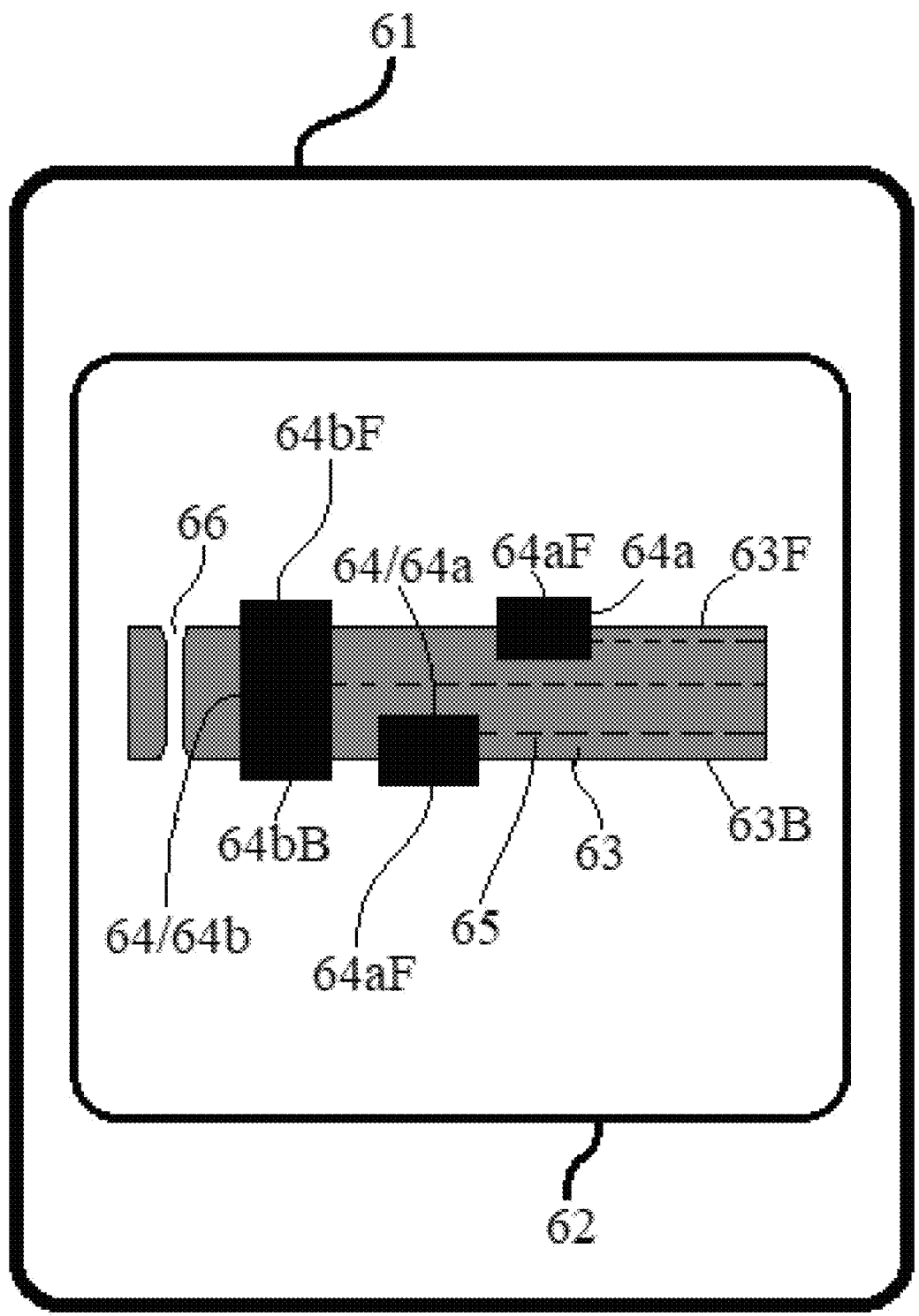
FIG. 1B schematically shows a medical device or system such as a neurostimulator or a neurostimulating system used in a method in accordance with an exemplary embodiment of the present invention.

As shown in FIG. 1B, a medical device or system 61 such as a neurostimulator or neurostimulating system may be used in the method, and may include an implantable electrode device or lead 62. Implantable electrode device 62 includes a flexible non-conductive flap 63, one or more electrodes 64 integrated with the flap, and one or more wires 65 (represented as broken lines) embedded within the flap 63 and connected to the one or more electrodes 64. The implantable electrode device 62 is configured to wrap around one, two or more biological targets (not shown), so that one of the electrodes 64 can electrically and stably contact one of the biological targets.

The flap 63 may have a front side 63F and a back side 63B. One of the electrodes 64a may have only one flat contacting surface 64aF that can electrically contact one of the biological targets. The contacting surface 64aF may be on the front side of the flap 63F, or on the back side of the flap 63B. Alternatively, one of the electrodes 64b may have only two flat contacting surfaces (64bF, 64bB) that can electrically contact one of the biological targets. One of the two contacting surfaces 64bF may be on the front side of the flap 63F, and another one 64bB is on the back side of the flap 63B, and vice versa.

In preferred embodiments, the flap 63 comprises one or more suture holes 66 (typically through holes) for stitching the flap 63 around the one, two or more biological targets.

In some embodiments where the flap comprises one or more suture holes for stitching the flap around the one or more nerves, the method may further include a step (iv-b) stitching the flap around the one or more nerves through the one or more suture holes.

Figure 2:
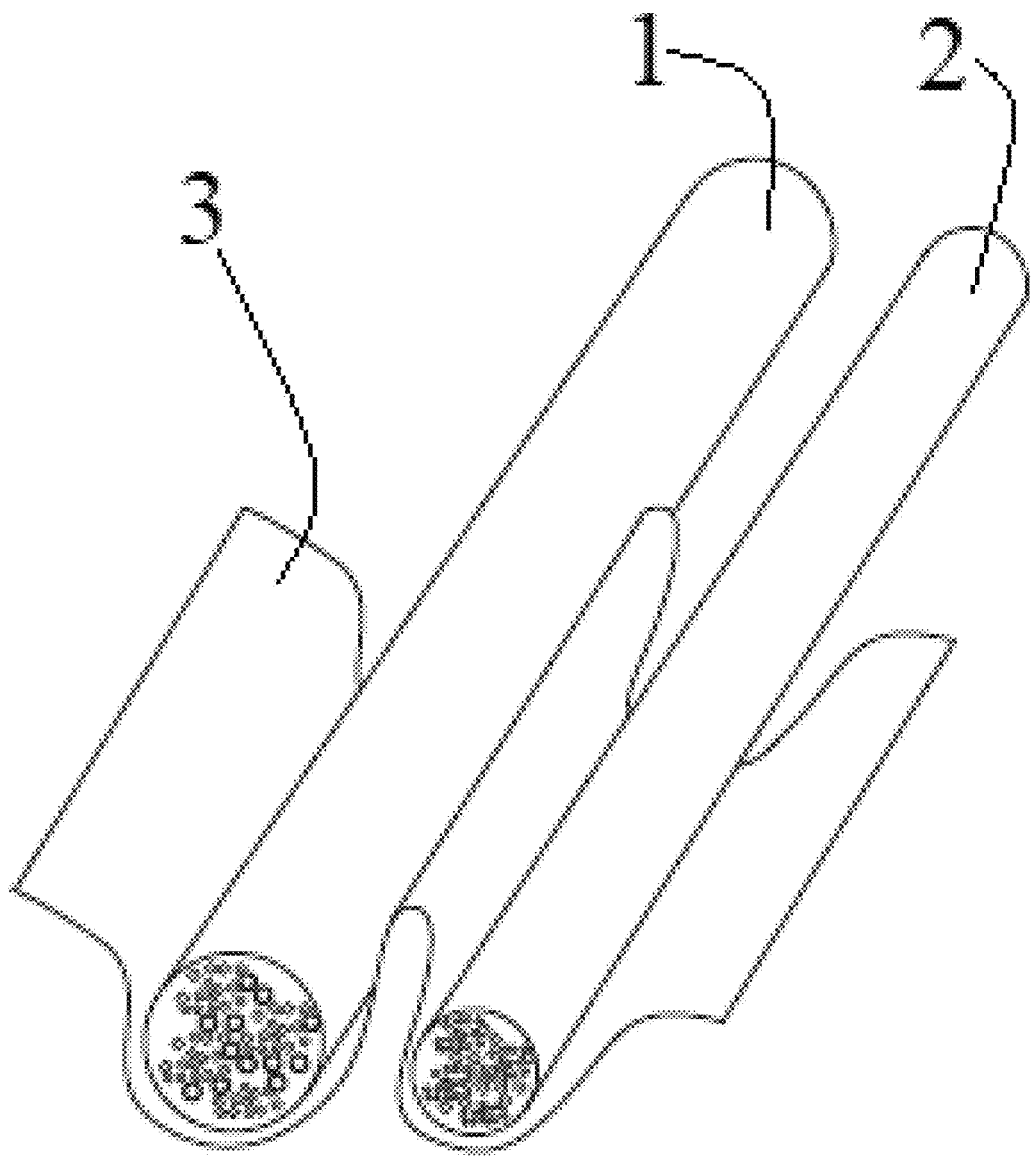
FIG. 2 shows a flap wrapped around (partially or completely) an anterior nerve bundle and a posterior nerve bundle in accordance with an exemplary embodiment of the present invention.

In various exemplary embodiments of the invention, an implantable lead is used to stimulate anterior and posterior spinal nerve components. FIG. 2 shows a flap wrapped around (partially or completely) an anterior nerve bundle and a posterior nerve bundle in accordance with an exemplary embodiment of the present invention. As shown in FIG. 2, the epineurium connecting the anterior nerve bundle 1 and posterior nerve bundle 2 is incised, separating the two nerve bundles from each other. Through the incision, flap 3 is wrapped around (partially or completely) the anterior nerve bundle 1 and posterior nerve bundle 2.

Figure 3:
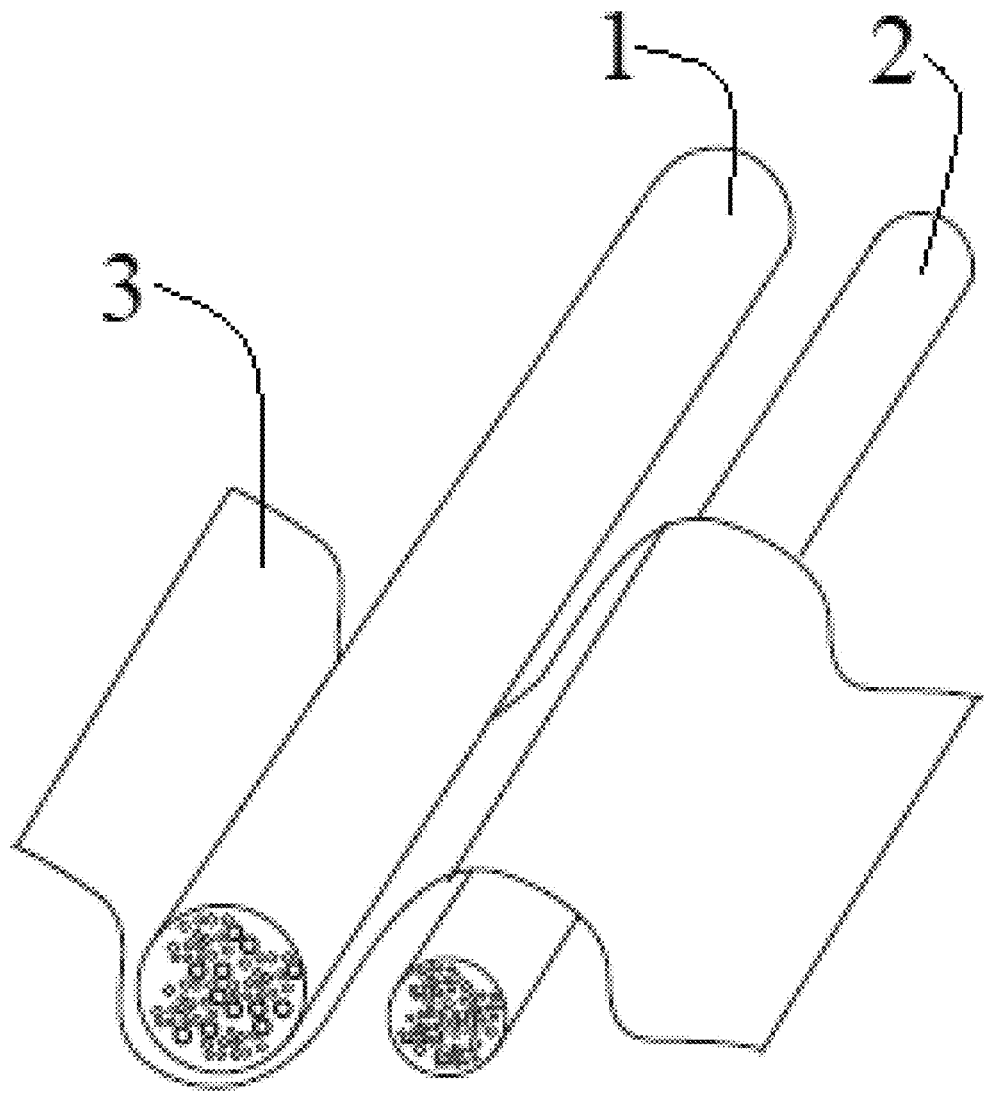
FIG. 3 illustrates electrodes on both sides of the flap are required to wrap around (partially or completely) an anterior nerve bundle and a posterior nerve bundle in accordance with an exemplary embodiment of the present invention.

FIG. 3 illustrates electrodes on both sides of the flap are required to wrap around (partially or completely) an anterior nerve bundle and a posterior nerve bundle in accordance with an exemplary embodiment of the present invention. FIG. 3 shows another embodiment in which electrodes on both sides of flap 3 are required.

Figure 4:
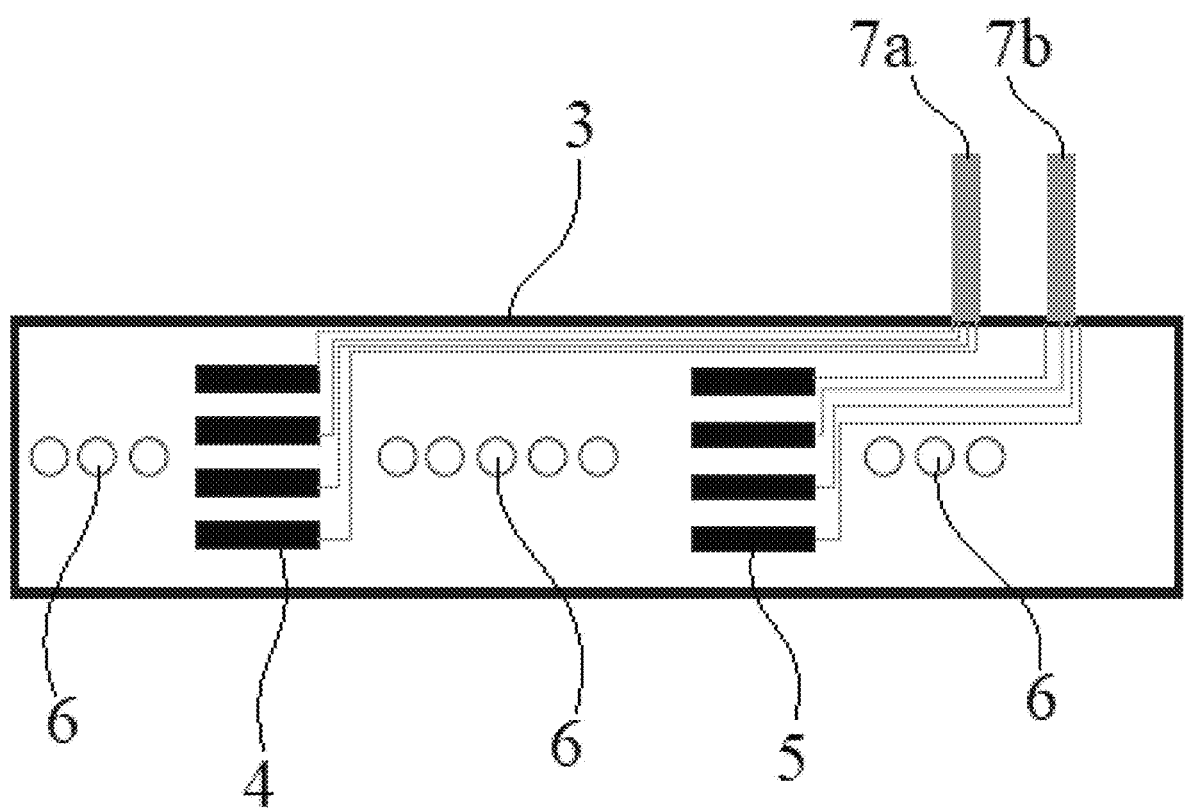
FIG. 4 demonstrates an implantable electrode device including microelectrode arrays and suture holes in accordance with an exemplary embodiment of the present invention.

FIG. 4 demonstrates an implantable electrode device including microelectrode arrays and suture holes in accordance with an exemplary embodiment of the present invention. The electrodes in the implantable electrode device of the invention may include microelectrodes. The flap may include one, two or more electrode blocks, and each block comprises an array of microelectrodes. For example, the flap comprises two or more electrode blocks, and the blocks are arranged linearly along an elongation direction of the flap. One, two or more suture holes may be located in the proximity of each block. For instance, two or more suture holes may be arranged linearly along an elongation direction of the flap to form a hole-segment, and each electrode block is flanked by one or two of such hole-segments. As shown in FIG. 4, reference number 4 refers to a first electrode block (or "Stimulation Contacts I"). Reference number 5 refers to a second electrode block (or "Stimulation Contacts II"). Reference number 6 refers to suture holes arranged in three hole-segments. Reference numbers 7a and 7b refer to connectors for wires. Stimulation Contact Blocks are not limited by individual contacts or stimulation blocks Such a flap 3 is like a clothing belt with holes 6 but without a frame-style buckle or a plate-style buckle. Electrodes, electrode blocks, or microelectrode arrays (e.g. 4 and 5) can be placed around belt holes 6, preferably between belt holes 6.

Figure 5:
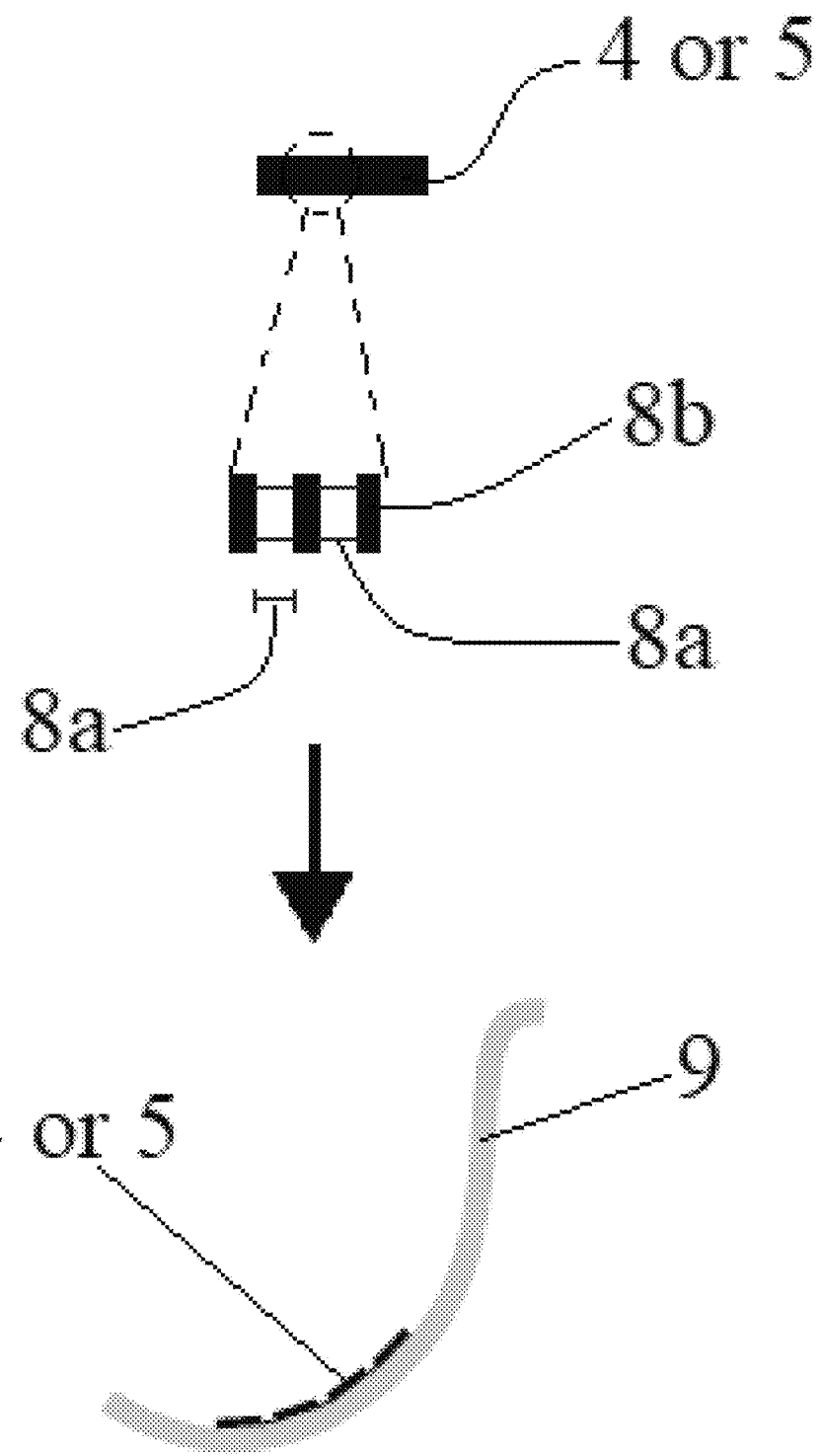
FIG. 5 depicts some details of a stimulation contact in accordance with an exemplary embodiment of the present invention.

FIG. 5 depicts some details of a stimulation contact in accordance with an exemplary embodiment of the present invention. FIG. 5 shows some details of stimulation contact 4/5. Reference number 8a refers to a bridge (actual distance is very small but exaggerated here for illustrative purposes) between two microelectrodes 8b. Reference number 9 refers to a nerve. Thin film (flap) with small bridge 8 connection allows flexibility of the contact 4 or 5 to shape around the nerve 9.

Figure 6:
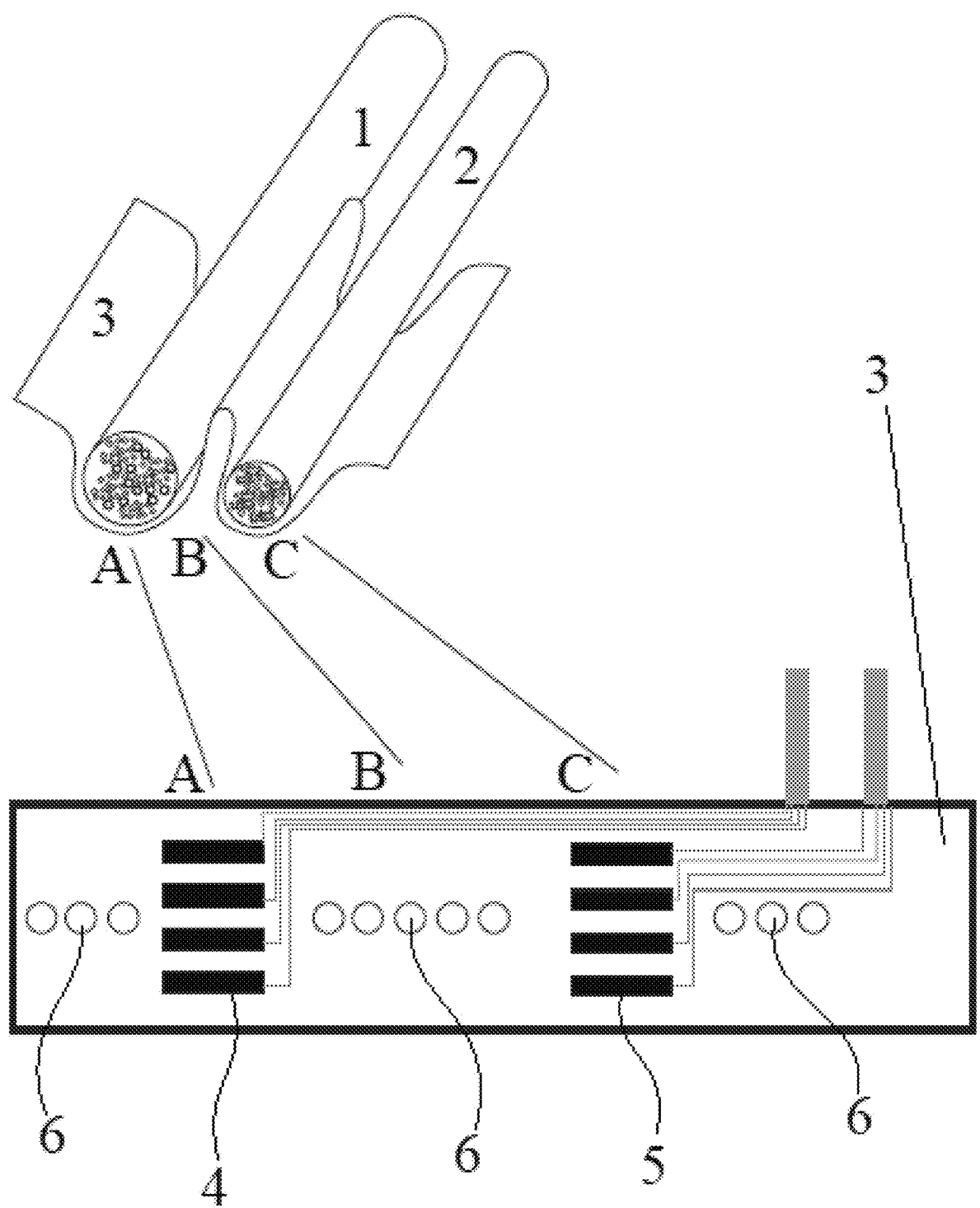
FIG. 6 illustrates the relationship between contacting areas in the flap and corresponding contacting areas in the nerves in accordance with an exemplary embodiment of the present invention.

FIG. 6 illustrates the relationship between contacting areas "A", "B" and "C" in the flap and corresponding contacting areas "A", "B" and "C" in the nerves.

Figure 7:
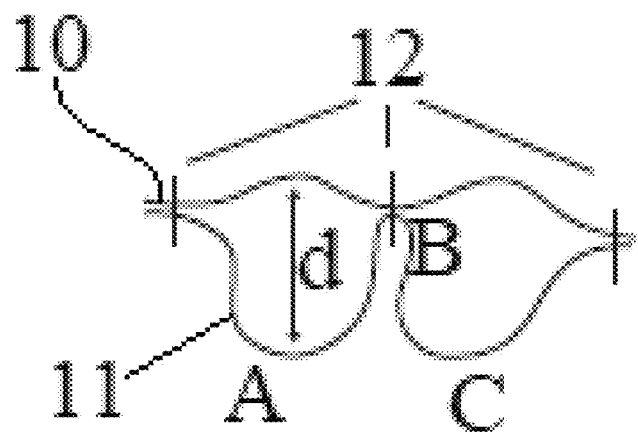
FIG. 7 schematically shows a manner how two flaps are wrapped around (partially or completely) an anterior nerve bundle and a posterior nerve bundle in accordance with an exemplary embodiment of the present invention.

FIG. 7 schematically shows a manner how two flaps are wrapped around (partially or completely) an anterior nerve bundle and a posterior nerve bundle in accordance with an exemplary embodiment of the present invention. In FIG. 7, reference number 10 refers to a top flap. Reference number 11 refers to a bottom flap. Reference number 12 refers to fixation points for suture, stitching, or clipping. Diameter d may be adjustable according to different nerve size.

Figure 8:
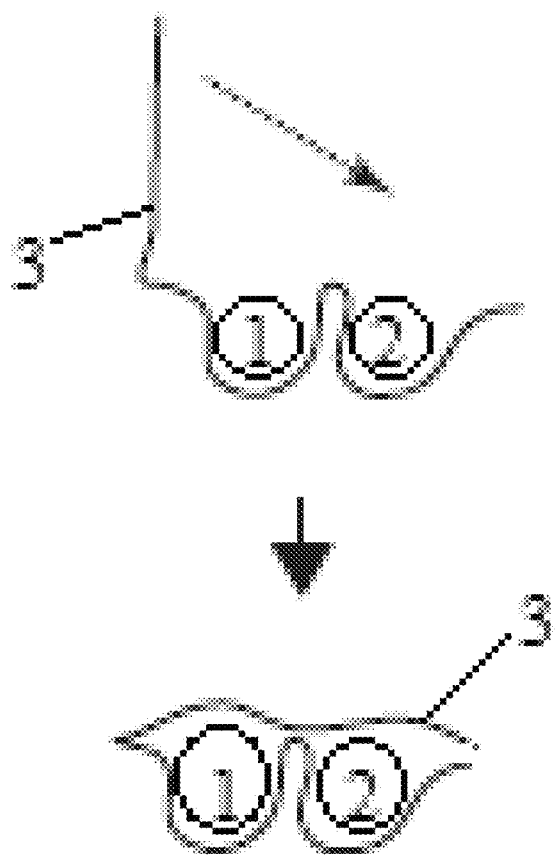
FIG. 8 schematically shows a manner how a single flap is wrapped around (partially or completely) an anterior nerve bundle and a posterior nerve bundle in accordance with an exemplary embodiment of the present invention.

FIG. 8 schematically shows a manner how a single flap is wrapped around (partially or completely) an anterior nerve bundle and a posterior nerve bundle in accordance with an exemplary embodiment of the present invention. FIG. 8 shows another method to cover and fix the stimulation lead by flipping a single flap on top.

In specific embodiments, the diagnostic and/or therapeutic method is a neurostimulating method for bladder control, and step (v) of executing a diagnostic and/or therapeutic process is executing a neurostimulation protocol for bladder control, providing a coordinated stimulation of anterior and posterior spinal nerve components for bladder control. The embodiments introduce a special electrode that will achieve a similar or better result without cutting nerves, as compared to the known technology. The blocking of the afferent nerves may be achieved by surgically separating the sacral spinal nerve into efferent (to the bladder) and afferent (to the spinal cord and brain) Using a stimulation protocol of the invention may be applied on the different nerve bundles. Efferent stimulation to create a bladder contraction and afferent nerve trunk to block the inhibition fibers.

Bladder evacuation in spinal cord injured patients may be accomplished via electrical nerve stimulation. Bladder and urethra are controlled from the brain traveling through the spinal cord to the sacrum and the final organs. Stimulating the entire sacral spinal nerve branch, containing the anterior ASN and posterior PSN nerve bundles results in a contraction of both, the bladder and the urethral outlet, effectively blocking the urine flow.

In a procedure, PSN are cut (irreversible rhizotomy) to suppress inhibitory nerve branches. ASN and PSN can be surgically separated after performing a laminectomy. This allows application of various independent stimulation and sensing (action potential) protocols on ASN and PSN for bladder evacuation and avoid a rhizotomy.

In various exemplary embodiments, stimulation protocols and waveforms specifically address the functions needed from the particular nerve branch. Examples of combinations include, but are not limited to the following: (1) stimulate ASN for bladder contractions+PSN to block nerve activity, (2) stimulate ASN+sense response on PSN: • generate optimized waveform for bladder contractions and Inhibition of PSN, (3) stimulate PSN+sense response on ASN: • generate optimized waveform for bladder contractions and inhibition of PSN; (4) applying alternating stimulation on PSN and ASN; (5) stimulated ASN and sense evoked potentials on ASN-1 to ASN-3 to detect latency differences, where large fibers have short and small sensory fibers have longer latencies: • analyze and develop stimulation protocols and waveforms to target specific nerve fiber to fire or to inhibited.

Figure 9:
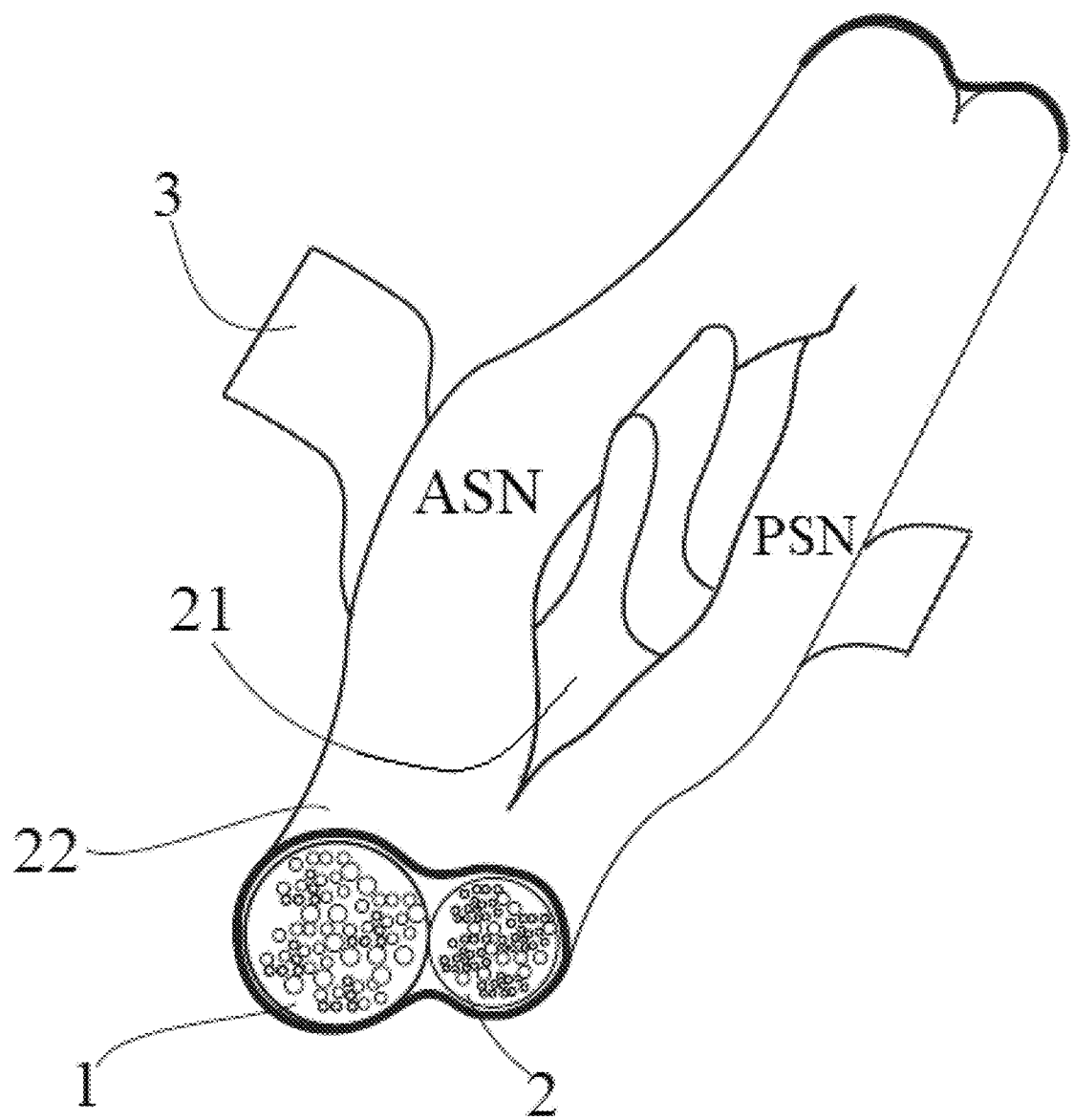
FIG. 9 demonstrates sacral spinal nerve exposed after sacral laminectomy in accordance with an exemplary embodiment of the present invention.

FIG. 9 shows sacral spinal nerve exposed after sacral laminectomy. Reference number 1 refers to anterior spinal nerve branch (ASN). Reference number 2 refers to posterior spinal nerve branch (PSN). Reference number 3 refers to a stimulation electrode (contacts and connections not shown). Reference number 21 refers to the incised epineurium separating anterior and posterior nerve bundles. Reference number 22 refers to the epineurium. The epineurium is the outermost layer of dense irregular connective tissue surrounding a peripheral nerve. It usually surrounds multiple nerve fascicles as well as blood vessels which supply the nerve.

Figure 10:
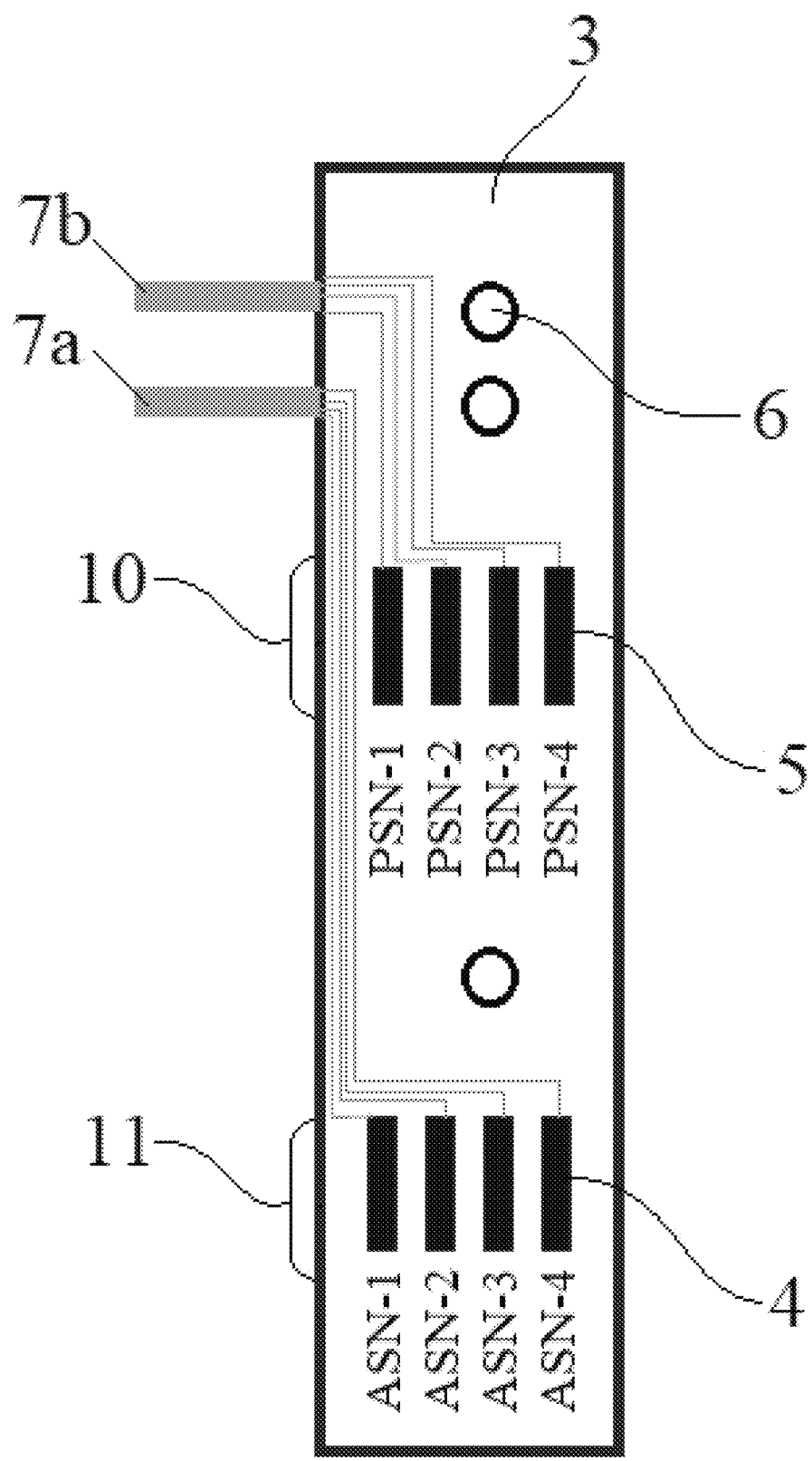
FIG. 10 illustrates an implantable electrode device with ASN and PSN stimulation contacts in accordance with an exemplary embodiment of the present invention.

In FIG. 10, reference number 3 refers to the flap. Reference numbers 7a and 7b refer to connectors. Reference number 10 refers to PSN stimulation location or area. Reference number 11 refers to ASN stimulation location or area. Reference number 5 refers to PSN stimulation contacts such as PSN-1, PSN-2, PSN-3 and PSN-4. Reference number 4 refers to ASN stimulation contacts such as ASN-1, ASN-2, ASN-3 and ASN-4. Stimulation Contact Blocks are not limited by individual contacts or stimulation blocks.

Figure 11:
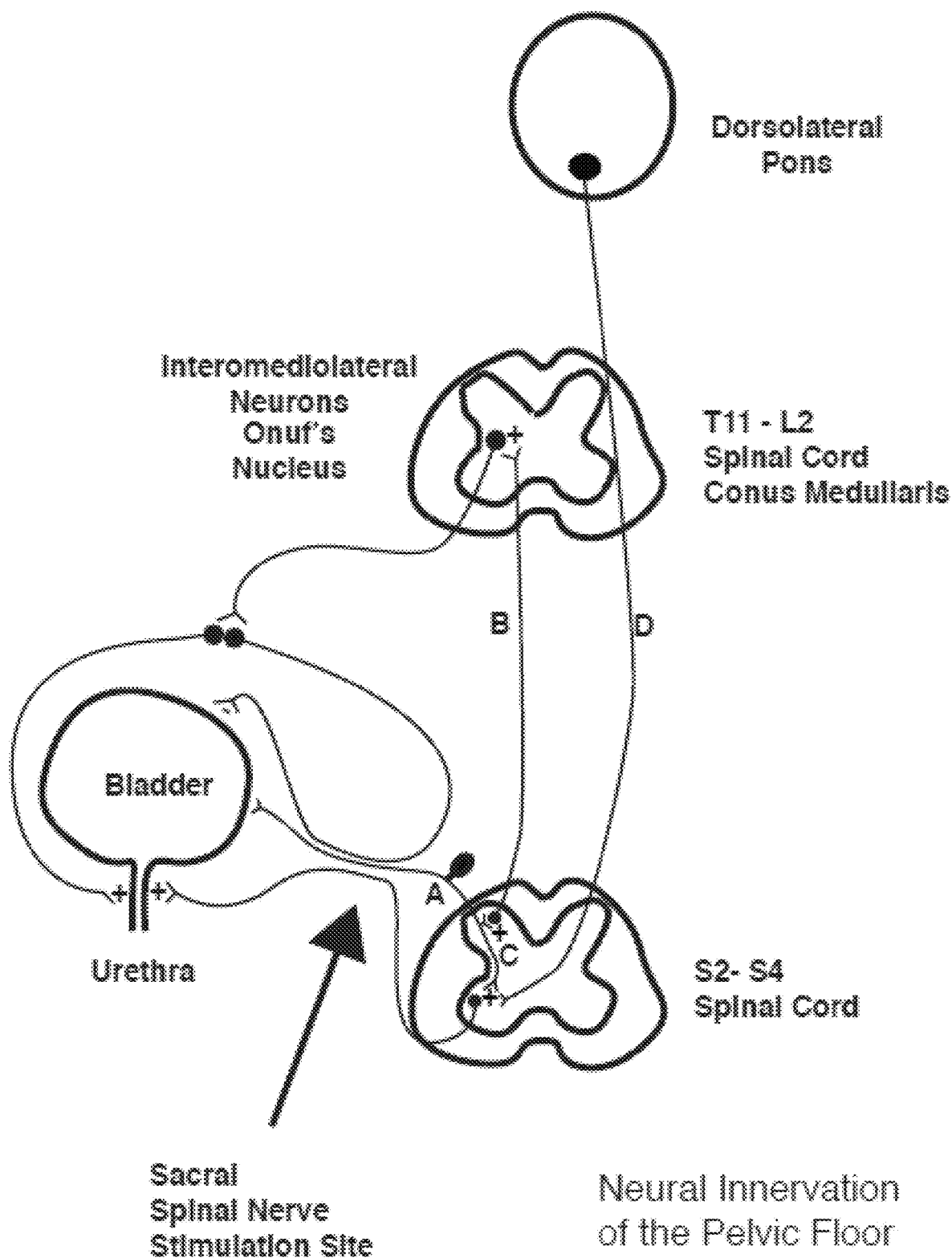
FIG. 11 schematically shows the neural innervation of the pelvic floor in accordance with an exemplary embodiment of the present invention.

FIG. 11 shows the neural innervation of the pelvic floor and includes the following components: bladder, urethra, dorsolateral pons, interomediolateral neurons onuf's nucleus, T11-L2 spinal cord conus medullaris, S2-S4 spinal cord; and sacral spinal nerve stimulation site.

In the foregoing specification, embodiments of the present invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicant to be the scope of the invention, is the literal and equivalent scope of the set of claims that issue from this application, in the specific form in which such claims issue, including any subsequent correction.

The invention claimed is:

1. A diagnostic and/or therapeutic method, comprising (i) providing a medical device or system comprising a flexible and implantable electrode device in a sacral area; (ii) determining or locating two or more biological targets in a patient, wherein the two or more biological targets are naturally integrated to each other; (iii) disintegrating and separating the two or more biological targets from each other; (iv) wrapping the electrode device around one or more of the separated biological targets, so that at least one electrode in the electrode device can electrically and stably contact the biological target(s); and (v) executing a diagnostic and/or therapeutic process on the biological target(s) by stimulating nerve branches in a coordinated way, preventing impulses of a posterior nerve branch to inhibit a bladder contraction.

2. The diagnostic and/or therapeutic method according to claim 1, wherein the two or more biological targets are naturally integrated to each other by connecting through a connective tissue.

3. The diagnostic and/or therapeutic method according to claim 1, wherein the two or more biological targets are naturally integrated to each other by encapsulating together inside a same confinement made of connective tissue.

4. The diagnostic and/or therapeutic method according to claim 3, wherein the two or more biological targets include an anterior segmental nerve (ASN) and a posterior segmental nerve (PSN) that are encapsulated together within an epineurium.

5. The diagnostic and/or therapeutic method according to claim 4, wherein the step (iii) of disintegrating and separating the two or more biological targets from each other is carried out by cutting the epineurium (e.g. a laminectomy).

6. The diagnostic and/or therapeutic method according to claim 5, wherein the method is a neurostimulation method for bladder control, wherein the step (v) of executing a diagnostic and/or therapeutic process is executing a neurostimulation protocol for bladder control.

7. The diagnostic and/or therapeutic method according to claim 1, wherein the implantable electrode device comprises a flexible non-conductive flap, one or more electrodes integrated with the flap, and one or more wires embedded within the flap and connected to the one or more electrodes, wherein the implantable electrode device is configured to wrap around one, two or more biological targets of said two or more biological targets in claim 1, so that one of the electrodes can electrically and stably contact one of said two or more biological targets in claim 1.

8. The diagnostic and/or therapeutic method according to claim 7, wherein the flap has a front side and a back side, wherein one of the electrodes has only one flat contacting surface that can electrically contact one of the biological targets, and wherein the contacting surface is on the front side of the flap, or on the back side of the flap.

9. The diagnostic and/or therapeutic method according to claim 7, wherein the flap has a front side and a back side, wherein one of the electrodes has only two flat contacting surfaces that can electrically contact one of the biological targets, and wherein one of the two contacting surfaces is on the front side of the flap, and another one is on the back side of the flap.

10. The diagnostic and/or therapeutic method according to claim 7, wherein the flap comprises one or more suture holes for stitching the flap around the one, two or more biological targets.

11. The diagnostic and/or therapeutic method according to claim 7, wherein the electrodes comprise microelectrodes, wherein the flap comprises one, two or more electrode blocks, and each block comprises an array of microelectrodes.

12. The diagnostic and/or therapeutic method according to claim 7, wherein the flap comprises two or more electrode blocks, and the blocks are arranged linearly along an elongation direction of the flap.

13. The diagnostic and/or therapeutic method according to claim 12, wherein the flap further comprises one, two or more suture holes located in the proximity of each block.

14. The diagnostic and/or therapeutic method according to claim 13, wherein two or more suture holes are arranged linearly along an elongation direction of the flap to form a hole-segment, and each electrode block is flanked by one or two hole-segments.

15. The diagnostic and/or therapeutic method according to claim 13, wherein the biological targets include one, two or more nerves, further comprising a step of (iv-b) stitching the flap around the one or more nerves through the one or more suture holes after step (iv) but before step (v).

16. The diagnostic and/or therapeutic method according to claim 7, wherein the flap further comprises one, two or more suture holes.

17. The diagnostic and/or therapeutic method according to claim 16, further comprising a step of (iv-b) stitching the flap around the one or more biological targets through the one or more suture holes after step (iv) but before step (v).

* * * * *